US007708685B2

(12) United States Patent
Okada

(10) Patent No.: US 7,708,685 B2
(45) Date of Patent: May 4, 2010

(54) OPERATING INSTRUMENT SYSTEM FOR ENDOSCOPE

(75) Inventor: Tsutomu Okada, Tachikawa (JP)

(73) Assignee: Olympus Corporation (JP)

( * ) Notice: Subject to any disclaimer, the term of this patent is extended or adjusted under 35 U.S.C. 154(b) by 1372 days.

(21) Appl. No.: 11/142,033

(22) Filed: May 31, 2005

(65) Prior Publication Data
US 2005/0288547 A1 Dec. 29, 2005
US 2006/0094927 A9 May 4, 2006

(30) Foreign Application Priority Data
Jun. 2, 2004 (JP) .............................. 2004-164420

(51) Int. Cl.
A61B 1/00 (2006.01)
(52) U.S. Cl. ...................... 600/106; 600/104
(58) Field of Classification Search ............... 600/101, 600/104, 106, 126, 131, 146, 149, 107, 153, 600/154
See application file for complete search history.

(56) References Cited

U.S. PATENT DOCUMENTS

| 4,797,737 | A | * | 1/1989 | Yazawa | ........................ 348/73 |
| 4,976,697 | A |   | 12/1990 | Walder et al. | |
| 5,431,645 | A | * | 7/1995 | Smith et al. | .................... 606/1 |
| 5,695,491 | A |   | 12/1997 | Silverstein | |
| 6,059,719 | A | * | 5/2000 | Yamamoto et al. | .......... 600/127 |
| 6,171,234 | B1 | * | 1/2001 | White et al. | ................. 600/102 |
| 6,371,907 | B1 | * | 4/2002 | Hasegawa et al. | ............ 600/146 |
| 7,276,044 | B2 | * | 10/2007 | Ferry et al. | .............. 604/95.01 |
| 7,371,210 | B2 | * | 5/2008 | Brock et al. | ................. 600/114 |

FOREIGN PATENT DOCUMENTS

| EP | 1 568 306 A1 | 8/2005 |
| JP | A-57-117823 | 7/1982 |
| JP | A-2000-000207 | 1/2000 |
| JP | A-2003-111769 | 4/2003 |

OTHER PUBLICATIONS

Search Report issued by European Patent Office on Sep. 21, 2005 in connection with corresponding European Application No. EP 05 01 1605.

* cited by examiner

Primary Examiner—John P Leubecker
Assistant Examiner—Victoria W Chen
(74) Attorney, Agent, or Firm—Ostrolenk Faber LLP

(57) ABSTRACT

An endoscope operating instrument system which includes a back-and-forth movement mechanism for providing a back-and-forth movement drive force required to operate a forceps located at a distal end of the operating instrument and an insertion/withdrawal mechanism designed to insert and withdraw the insert section via an endoscope channel. A winding unit for winding the insert section of the operating instrument is provided and the insertion/withdrawal mechanism is adapted to insert and withdraw the insert section by rotating the winding unit together with the back-and-forth movement mechanism. Thus, a compact system structure is obtained.

6 Claims, 6 Drawing Sheets

OPERATING INSTRUMENT SYSTEM FOR ENDOSCOPE

CROSS-REFERENCE TO RELATED APPLICATION

This application is based upon and claims the benefit of priority from the prior Japanese Patent Application No. 2004-164420, filed on Jun. 2, 2004, the entire contents of which application are incorporated herein by reference.

BACKGROUND OF THE INVENTION

1. Field of the Invention

The present invention relates to an operating instrument system for an endoscope.

2. Description of the Related Art

Since an operating instrument system for an endoscope has a long insert section (an insert section of the operating instrument), handling of the insert section of the operating instrument gives an operator a lot of trouble when inserting the same through an endoscope channel into a body cavity. Therefore, an endoscope provided with a mechanized insertion/withdrawal device for inserting and withdrawing the operating instrument automatically from an operating instrument insertion port of the endoscope has been proposed, for example, as shown in FIG. 1 of JP-A-57-117823.

There is also proposed an endoscope provided with an operating instrument drive unit separately from an endoscope body and the operating instrument, which is operated by engaging an operating unit of the operating instrument with the operating instrument drive unit and operated by a foot switch that enables the operation of the operation instrument to be performed electrically by the operator of the endoscope. For an example, see FIG. 1 in JP-A-2003-111769.

There is also proposed an endoscope which is operated by connecting a power pack and a foot switch, which are provided separately from the endoscope, to a power unit, which is detachably attached to the endoscope. For example, see FIG. 6 and FIG. 8 in JP-A-2000-207.

BRIEF SUMMARY OF THE INVENTION

An operating instrument system for an endoscope according to the invention includes a back-and-forth movement mechanism for providing a back-and-forth drive force required for operating a distal end of an operating instrument, and an insertion/withdrawal mechanism for inserting and withdrawing an insert section of the operating instrument into/from an endoscope channel. The system is configured to provide a winding unit for winding the insert section of the operating instrument, and the back-and-forth movement drive mechanism carries out insertion and withdrawal of the insert section of the operating instrument by rotating the winding unit in association with the back-and-forth movement mechanism.

For example, the insert section of the operating instrument is flexible, and includes a sheath pipe connected at a proximal side with the winding unit and a drive force transmitting member (for example, an operating wire) capable of advancing and retracting with respect to the sheath pipe and the winding unit and transmitting a drive force to the distal end of the operating instrument.

In this case, the winding unit may include a first connecting member for connecting the sheath pipe and the back-and-forth movement drive mechanism, and a second connecting member which connects the drive force transmitting member and the back-and-forth movement drive mechanism and which is movable relative to the first connecting member.

The back-and-forth movement drive mechanism may include a first operating unit which can be connected to the first connecting member, and a second operating unit which can be connected to the second connecting member and is capable of moving relative to the first operating unit.

The insertion/withdrawal mechanism may be detachably attached to the endoscope.

It is also possible to provide a manual operating unit which enables manual rotation of the back-and-forth movement drive mechanism with respect to the insertion/withdrawal mechanism.

Alternatively, it is possible to provide an electric contact point for electrically connecting the back-and-forth movement drive mechanism and the insertion/withdrawal mechanism and a power pack for supplying a drive power for driving the second operating unit to the back-and-forth movement drive mechanism via the electric contact point on the endoscope to configure an electric endoscope.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF THE DRAWINGS

Preferred embodiments will be described below with reference to the accompanying drawings.

Figure 1:
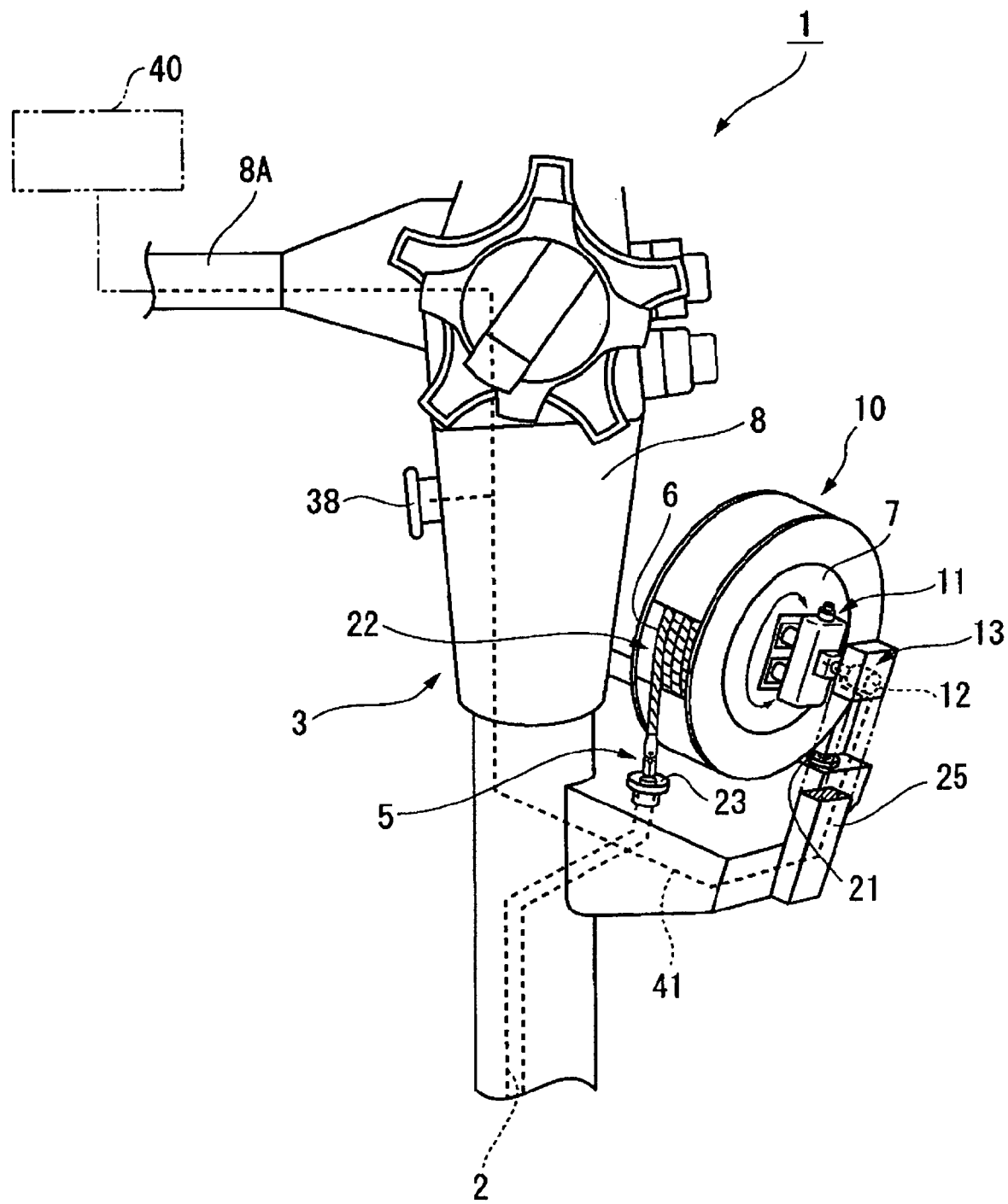
FIG. 1 is a perspective view showing an operating instrument system for an endoscope according to a first embodiment of the invention.
Figure 2:
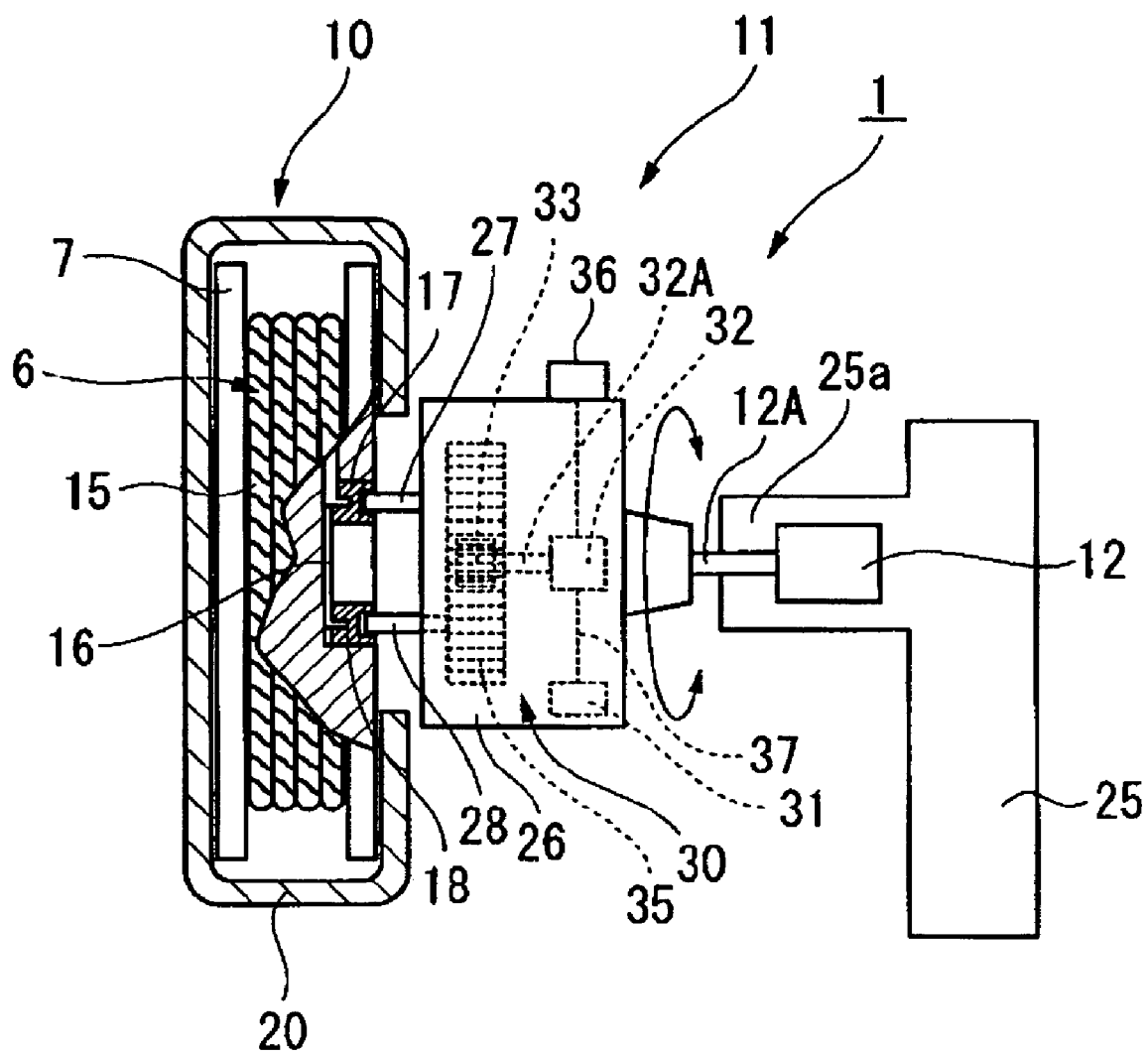
FIG. 2 is an enlarged view, partly in cross section, of a principal portion of the operating instrument system for an endoscope according to the first embodiment of the present invention.

Referring now to FIG. 1 and FIG. 2, a first embodiment will be described.

An operating instrument system 1 for an endoscope according to this embodiment includes an endoscope 3, a forceps insert section 6 (insert section of the operating instrument) a storage unit 10, a back-and-forth movement drive mechanism 11, and an insertion/withdrawal mechanism 13. The endoscope 3 includes a channel 2. The forceps insert section 6 includes a distal end of the forceps (distal end of operating instrument) 5 for conducting treatment by opening and closing the forceps responsive to a supply of a predetermined back-and-forth movement drive force. It can be inserted into the channel 2. The storage unit 10 includes a winding unit 7 to which a proximal side of the forceps insert section 6 is connected so as to be capable of winding the same. The storage unit is detachably attached to an operating unit 8 of the endoscope 3. The back-and-forth movement drive mechanism 11 is connected to the winding unit 7 and supplies the back-and-forth drive force to the distal end 5 of the forceps so as to open and close the distal end 5 of the forceps. The insertion and withdrawal mechanism 13 inserts and withdraws the forceps insert section 6 into and out of the channel 2. The insertion/withdrawal mechanism 13 includes an insertion and withdrawal motor (rotary drive) 12 for causing the back-and-forth movement drive mechanism 11 connected to the winding unit 7 to rotate with the winding unit 7 about a revolving shaft of the winding unit 7.

The insert section 6 for the forceps is provided with a sheath pipe 15 and an operation wire (drive force transmitting member) 16. The sheath pipe 15 is flexible and is connected at the proximal side to the winding unit 7. The operation wire 16 is inserted through the sheath pipe 15 and is capable of moving back-and-forth with respect to the sheath pipe 15 and the winding unit 7 so as to transmit a drive force to the distal end 5 of the forceps.

The winding unit 7 is formed into a drum shape, and the forceps insert section 6 can be wound on the outer peripheral surface thereof. A first connecting member 17 and a second connecting member 18 to which a proximal end of the operation wire 16 is connected are disposed on the side surface of the winding unit 7. The first connecting member 17 connects the sheath pipe 15 and the back-and-forth movement drive mechanism, while the second connecting member 18 is capable of moving with respect to the first connecting member 17. In this arrangement, the positional relation between the first connecting member 17 and the proximal end of the sheath pipe 15 is fixed, and the positional relation between the second connecting member 18 and the proximal end of the operation wire 16 is fixed.

The storage unit 10 includes a case 20 formed larger than the outer diameter of the winding unit 7 and covering the winding unit 7 so as to be capable of rotating freely therein, and also including a mounting member 21 which can be mounted to the operating unit 8 near a forceps port 23 of the endoscope 3. The case member 20 is provided with an opening 22 for allowing access of the forceps insert section 6.

The back-and-forth movement drive mechanism 11 projects from one end 25a of the supporting member 25, which is disposed at a position opposing to the operating unit 8 with the intermediary of the forceps port 23 of the endoscope 3. The back-and-forth movement drive mechanism 11 includes an enclosure 26, a first operating unit 27, a second operating unit 28, a back-and-forth movement mechanism 30, and a power pack 31. The enclosure 26 is connected to the insertion/withdrawal mechanism 13. The first operating unit 27 is fixed to the enclosure 26, and is capable of connecting with the first connecting unit 17 of the winding unit 7. The second operating unit 28 can be connected to the second connecting member 18 of the winding unit 7 and can move relative to the first operating unit 27. The back-and-forth movement mechanism 30 moves the second operating unit 28. The power pack 31 supplies drive power to the back-and-forth movement mechanism 30 for driving the second operating unit 28.

The back-and-forth movement mechanism 30 includes a back-and-forth movement motor 32, a back-and-forth movement revolving shaft 32A connected to the back-and-forth movement motor 32, and a pinion member 33 connected to the back-and-forth movement revolving shaft 32A. The back-and-forth movement mechanism 30 further includes a rack member 35 which is connected to the second operating unit 28 so as to engage with the outer peripheral surface of the pinion member 33, and a back-and-forth movement switch 36 that provides a drive instruction to the back-and-forth movement motor 32. The power pack 31 and the back-and-forth movement motor 32 are connected by a back-and-forth movement wiring 37.

The insertion/withdrawal motor 12 of the insertion and withdrawal mechanism 13 is disposed at one end 25a of the supporting member 25, and is provided with an insertion and withdrawal motor shaft 12A which connects the insertion and withdrawal motor 12 and the enclosure 26. The insertion and withdrawal mechanism 13 further includes an insertion and withdrawal switch 38, an insertion/withdrawal power pack 40, and insertion/withdrawal wiring 41. The insertion and withdrawal switch 38 is disposed on the operating unit 8 of the endoscope 3 to provide a drive instruction to the insertion/withdrawal motor 12. The power pack 40 is disposed at a position spaced from the endoscope 3 via a universal cord 8A, and supplies drive power to the insertion/withdrawal motor 12. The insertion/withdrawal wiring connects the insertion/withdrawal switch 38 and the insertion/withdrawal motor 12.

The operating method, effects, and advantages of the operating instrument system 1 for an endoscope according to this embodiment will now be described.

An operator mounts the storage unit 10 to the endoscope 3. At this time, the storage unit is in a state in which the proximal side of the forceps insert section 6 is wound around the winding unit 7, and the distal end 5 of the forceps projects from the opening 22 of the case member 20. The operator connects the first connecting member 17 of the winding unit 7 and the first operating unit 27 of the back-and-forth movement drive mechanism 11, and connects the second connecting member 18 of the winding unit 7 and the second operating unit 28 of the back-and-forth movement drive mechanism 11.

Subsequently, the operator inserts the distal side of the endoscope 3 into a body cavity.

When performing a biopsy, the operator holds the forceps insert section 6 projecting from the opening 22 of the case member 20, and operates the insertion/withdrawal switch 38 to a state in which the distal end 5 of the forceps is being directed to the forceps port 23. Then, the insertion/withdrawal motor 12 is activated to rotate the insertion/withdrawal motor shaft 12A, and to rotate the enclosure 26 of the back-and-forth movement drive mechanism 11 in the direction in which the forceps insert section 6 is being fed from the storage unit 10. The rotation is transmitted to the winding unit 7 via the first connecting member 17 and the second connecting member 18, whereby the winding unit 7 rotates with respect to the case member 20, and the forceps insert section 6 is fed into the channel 2.

The operator causes the distal end 5 of the forceps to project from the distal end of the endoscope 3 to reach a desired position, and then operates the insertion/withdrawal switch 38 to stop the driving of the insertion/withdrawal motor 12 to stop the rotation of the winding unit 7.

Then, the operator activates the back-and-forth movement switch 36 to rotate the back-and-forth movement motor 32. This causes the pinion member 33 to rotate with the back-and-forth movement revolving shaft 32A, and the rack member 35 engaged therewith moves the second operating unit 28 toward the first operating unit 27. As described above, the first connecting member 17 of the winding unit 7 is connected to the first operating unit 27 of the back-and-forth movement drive mechanism 11, and the sheath pipe 15 is connected to the first connecting member 17 via the winding unit 7. The second connecting member 18 of the winding unit 7 is connected to the second operating unit 28 of the back-and-forth movement drive mechanism 11 and the operation wire 16 is connected to the second connecting member 18. Therefore, as a result of movement of the second operating unit 28 toward the first operating unit 1, the operation wire 16 advances with respect to the sheath pipe 15 to cause the distal end 5 of the forceps to open.

When a desired tissue is reached, the operator operates the back-and-forth movement switch 36 and causes the back-and-forth movement motor 32 in the direction opposite from the direction described above to move the rack member 35 in the opposite direction. Then, the second operating unit 28 moves in the direction away from the first operating unit 27, whereby the operation wire 16 retracts toward the proximal side with respect to the sheath pipe 15, and the distal end 5 of the forceps closes to pinch the tissue.

When sampling the tissue, the operator operates the insertion/withdrawal switch 38 to cause the insertion and withdrawal motor 12 to rotate in the direction opposite from the rotation described above in a state in which the distal end 5 of the forceps is closed. Consequently, the enclosure 26 of the back-and-forth movement drive mechanism 11 rotates in the direction to pull the forceps insert section 6 into the storage unit 10.

At this time, the tissue pinched by the distal end 5 of the forceps is torn off for sampling, in response to the movement of the distal end 5 of the forceps. Then, the forceps insert section 6 is drawn out from the channel 2 as it is wound on the winding unit 7, and stored into the storage unit 10.

Thus, in the operating instrument system 1, the back-and-forth movement drive mechanism 11 and the sheath pipe 15 are connected by connecting the first operating unit 27 of the back-and-forth movement drive mechanism 11 and the first connecting member 17 of the winding unit 7. The back-and-forth movement drive mechanism 11 and the operation wire 16 are connected by connecting the second operating unit 28 of the back-and-forth movement drive mechanism 11 and the second connecting member 18 of the winding unit 7. Then, by moving the second operating unit 28 relatively with respect to the first operating unit 27, the operation wire 16 can be moved back-and-forth with respect to the sheath pipe 15, whereby the operation (opening/closing) of the distal end 5 of the forceps is achieved.

Also, by driving the insertion/withdrawal mechanism 13 and rotating the back-and-forth movement drive mechanism 11, the insert section 6 wound on the winding unit 7 of the storage unit 10 can be moved into and out of the channel 2.

In this manner, with the operating instrument system 1 for an endoscope of this embodiment, both operations of electric insertion/withdrawal of the forceps insert section 6 with respect to the endoscope 3 and the automatic opening and closing operation of the distal end 5 of the forceps are achieved at a location on the endoscope body near the operator, using a compact structure.

In addition, since the power pack 31 is disposed on the back-and-forth movement drive mechanism 11, it is not necessary to supply electric power from the insertion and withdrawal mechanism 13 to the back-and-forth movement drive mechanism 11, and hence the structure of the endoscope 3 is simplified.

Presently, referring to FIG. 3 and FIG. 4, the second embodiment will be described.

The components as in the first embodiment described above are represented by the same reference numerals and the description thereof is omitted.

The different points of the second embodiment from the first embodiment is that the power pack is integrated in the back-and-forth movement drive mechanism in the first embodiment, but the power pack is not integrated in the back-and-forth movement drive mechanism in the second embodiment. More specifically, an endoscope 43 is an operating instrument system 42 for an endoscope according to the second embodiment is provided with an electric contact point 46 which electrically connects the back-and-forth movement drive mechanism 45 and the insertion and withdrawal mechanism 13. Then, a power pack 47 for supplying drive power for driving the second operating unit 28 to the back-and-forth movement drive mechanism 45 through the electric contact point 46 is disposed at a position apart from the endoscope 43 in the same manner as the insertion/withdrawal power pack 40.

Figure 3A:
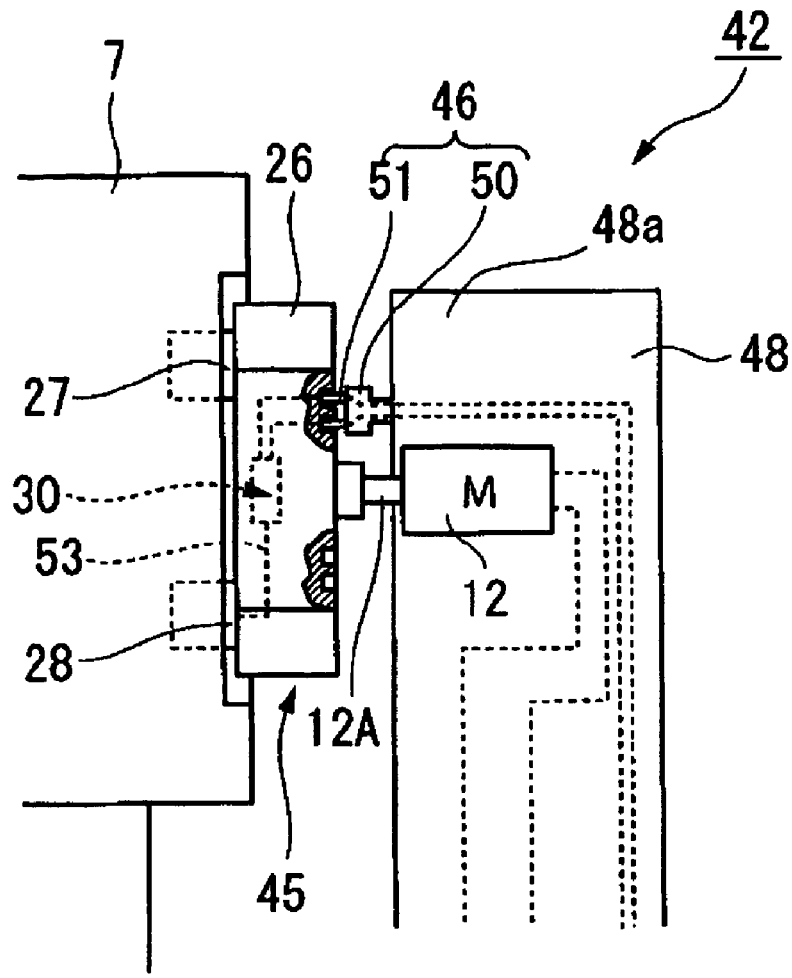
FIG. 3A is a partly cross-sectional view showing the operating instrument system for an endoscope according to a second embodiment of the invention.
Figure 3B:
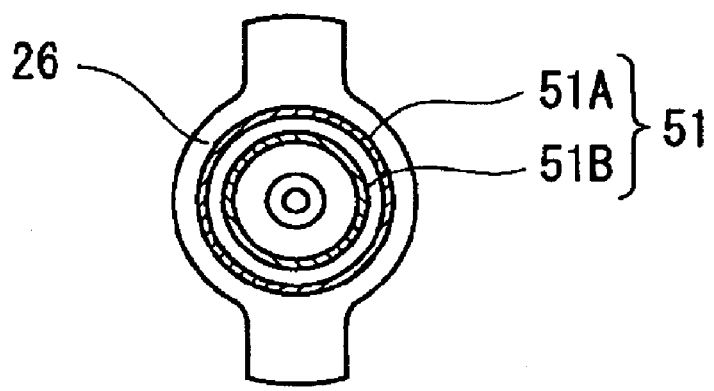
FIG. 3B is an enlarged view of a main portion showing a section of a contact point.
Figure 4:
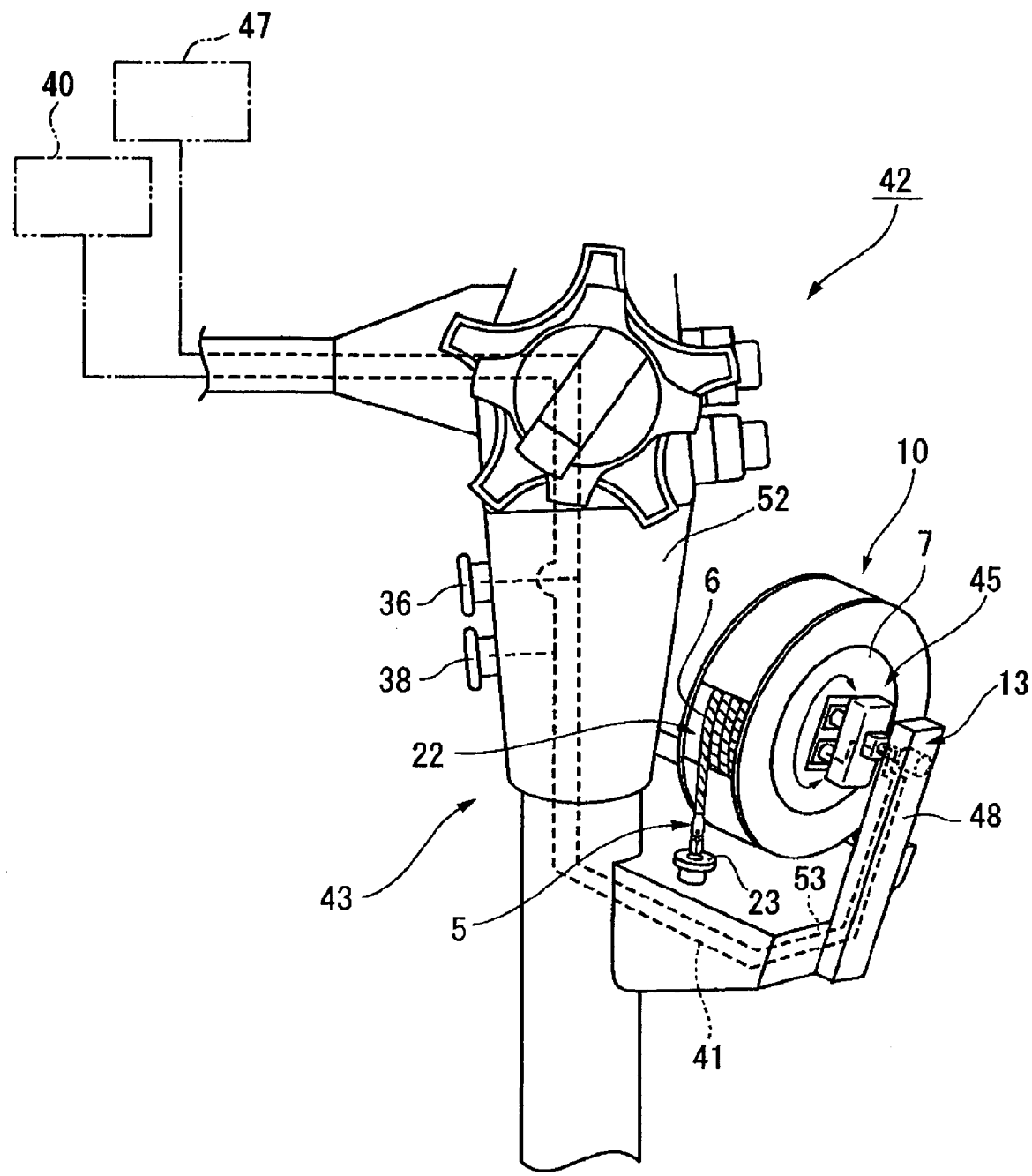
FIG. 4 is a perspective view showing the operating instrument system for an endoscope according to the second embodiment of the invention.
Figure 5A:
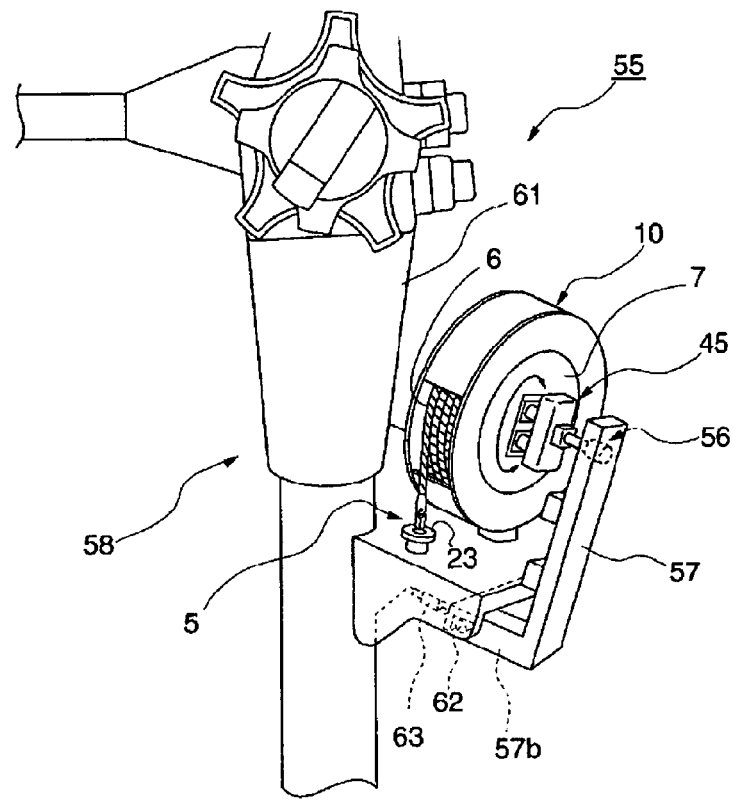
FIGS. 5A to 5C are perspective views showing the operating instrument system for an endoscope according to a third embodiment of the invention.
Figure 5B:
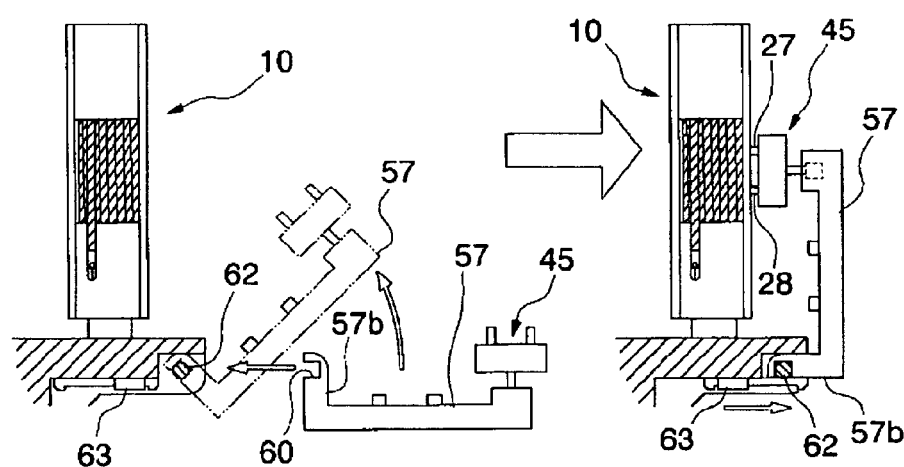
Figure 5C:
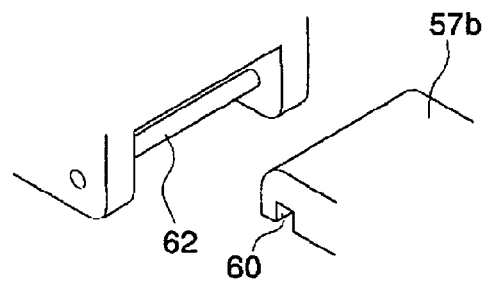
Figure 6:
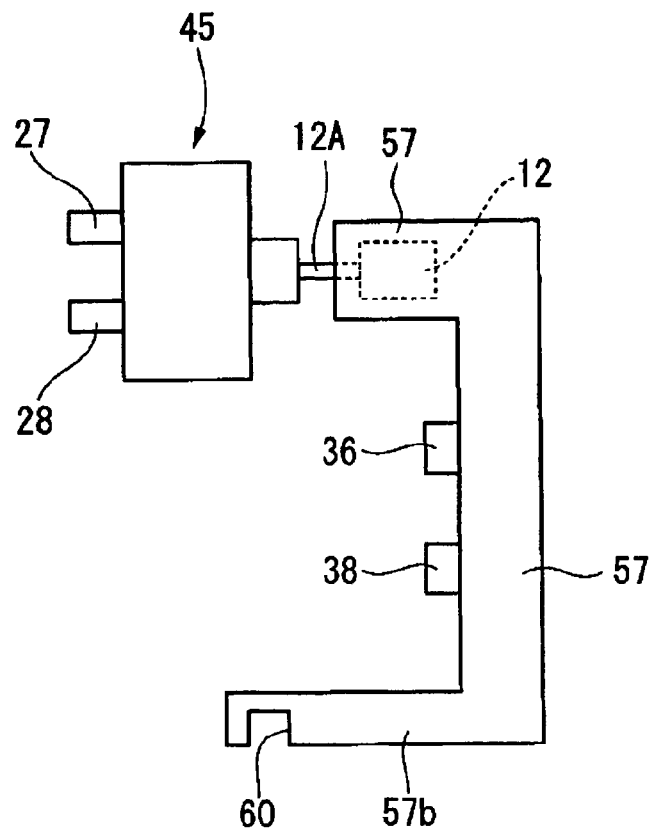
FIG. 6 is a side view showing a main portion of the operating instrument system for an endoscope according to the third embodiment of the invention.

The electric contact point 46 is provided with a fixed contact point 50 which projects from one end 48a of a supporting member 48 and a movable contact point 51 disposed on the enclosure 26 of the back-and-forth movement drive mechanism 45 as shown in FIG. 3A. The movable contact point 51 is formed as concentric grooves 51A, 51B in which the enclosure 26 of the back-and-forth movement drive mechanism 45 can turn with the fixed contact point 50 kept in contact as shown in FIG. 3B.

The back-and-forth movement switch 36 is disposed on an operating unit 52 adjacent to the insertion/withdrawal switch 38. A back-and-forth movement wiring 53 is provided not only in the enclosure 26, but also in the supporting member 48 via the electric contact point 46.

The system 42 according to the second embodiment provides the same effects and advantages through the operating method thereof as obtained from the operating instrument system 1 according to the first embodiment. However, since the power pack 47 is not located within the endoscope 43, the structure of the back-and-forth movement drive mechanism 45 is simplified.

Next, referring to FIGS. 5A-C and FIG. 6, a third embodiment will be described.

The same components as in the other embodiments described above are represented by the same reference numerals and the description thereof is omitted.

The third embodiment differs from the second embodiment is that the other end 57b of a supporting member 57 on which an insertion/withdrawal mechanism 56 of an operating instrument system 55 according to this embodiment is disposed is detachably attached to an endoscope 58.

The other end 57b of the supporting member 57 is provided with a hooking device 60 formed with a recess, which is engageable with a rod member 62 disposed on an operating unit 61 of the endoscope 58.

A holding member 63 for maintaining the engaged state between the hooking device 60 and the rod member 62 when the supporting member 57 is mounted to the endoscope 58 is provided near the rod member 62.

The back-and-forth movement switch 36 and the insertion/withdrawal switch 38 are disposed on the supporting member 57.

The operating method, effects, and advantages of the operating instrument system 55 according to the third embodiment will now be described.

The operator engages the hooking device 60 of the supporting member 57 with the rod member 62, and then mounts the supporting member 57 to the operating unit 61 by operating the holding member 63.

Subsequently, the operator mounts the storage unit 10 to the endoscope 58 via the mounting member 21 (FIG. 1), and connects the first connecting member 17 and the first operating unit 27, and the second connecting member 18 and the second operating unit 28.

Thereafter, the operator follows the same operation as in the second embodiment to carry out a treatment.

The operating instrument system 55 obtains the same effects and advantages as in the other embodiments described above. However, when such a treatment is not to be performed, the supporting member 57 can be detached from the endoscope 58 together with the insertion/withdrawal mechanism 56 by releasing the holding member 63. Therefore, handling of the endoscope 58 is facilitated. When repairing the insertion/withdrawal mechanism 56, only the insertion/withdrawal mechanism 56 will need to be handled.

Figure 7:
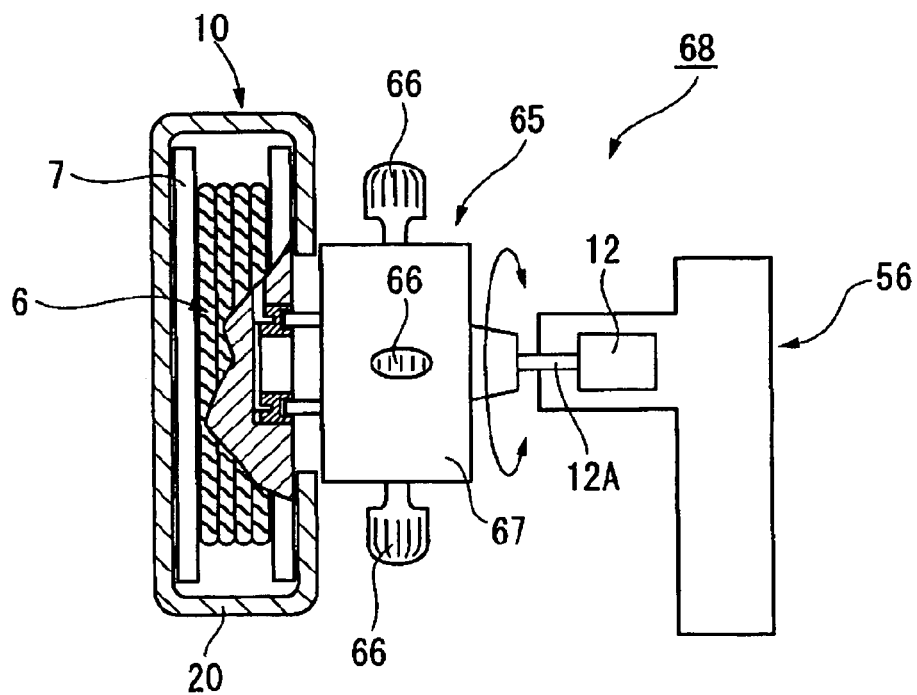
FIG. 7 is an enlarged drawing, partly in cross section, of a main portion of the operating instrument system for an endoscope according to another embodiment of the invention.

As shown in FIG. 7, it is also possible to configure an endoscope operating instrument system 68 in such a manner that manual operating devices (knobs) 66, which can rotate a back-and-forth movement drive mechanism 65 with respect to the insertion/withdrawal mechanism 56 by manual operation are disposed on the outer peripheral surface of an enclosure 67 of the back-and-forth movement drive mechanism 65 in the range not exceeding the outer diameter of the case member 20.

In this case, when fine back-and-forth movements of the forceps insert section 6 is required, the operator can adjust the length of insertion and withdrawal of the insert section 6 finely by operating the manual operating devices 66 and rotating the back-and-forth movement drive mechanism 65 in small steps.

While there has been shown and described what is considered to be preferred embodiments of the invention, it will, of course, be understood that various modifications and changes in form or detail could readily be made without departing from the sprit of the invention. It is therefore intended that the invention be not limited to the exact forms described and illustrated, but should be constructed to cover all modifications that may fall within the scope of the appended claims.

What is claimed is:

1. An operating instrument system for an endoscope, comprising:
    an operating instrument having an insert section insertable into and out of a channel of the endoscope, the operating instrument comprising a distal operating end which is responsive to a back-and-forth movement drive force;
    a storage unit for accommodating the operating instrument comprising a winding unit with a rotation axis, the winding unit being connected to a proximal end of the insert section so that the insert section of the operating instrument can be wound therearound,
    a back-and-forth drive mechanism detachably connected to the winding unit and providing the back-and-forth drive force to the distal operating end of the operating instrument, and
    an insertion/withdrawal mechanism provided with or mounted on the endoscope, comprising a rotary drive unit having a driving shaft on which the back-and-forth driving mechanism is provided at the distal end thereof;
    wherein the driving shaft of the insertion/withdrawal mechanism and the rotation axis of the winding unit are aligned so that the rotation of the driving shaft of the insertion/withdrawal mechanism is capable of rotating the winding unit through the back-and-forth movement drive mechanism about a revolving shaft of the winding unit to insert and withdraw the insert section into or from the channel.

2. The operating instrument system according to claim 1, wherein the insert section of the operating instrument comprises: a flexible sheath pipe connected at a proximal side to the winding unit; and a drive force transmitting member capable of moving back and forth with respect to the sheath pipe and the winding unit, to transmit the drive force to the distal operating end of the operating instrument, and
    wherein the winding unit comprises: a first connecting member for connecting the sheath pipe and the back-and-forth movement drive mechanism; and a second connecting member for connecting the drive force transmitting member and the back-and-forth movement drive mechanism and being movable relative to the first connecting member.

3. The operating instrument system according to claim 2, wherein the back-and-forth movement drive mechanism comprises: a first operating unit which can be connected to the first connecting member; and a second operating unit connectable to the second connecting member and movable relative to the first operating unit.

4. The operating instrument system according to claim 1, comprising a manual operating device capable of rotating the back-and-forth movement drive mechanism with respect to the insertion/withdrawal mechanism by manual operation.

5. The operating instrument system according to claim 3, wherein the back-and-forth movement drive mechanism comprises a power pack for supplying a drive power for driving the second operating unit.

6. The operating instrument system according to claim 3, wherein the endoscope comprises an electric contact for electrically connecting the back-and-forth movement drive mechanism and the insertion/withdrawal mechanism; and a power pack for supplying drive power for driving the second operating unit via the electric contact to the back-and-forth movement drive mechanism.

* * * * *